United States Patent [19]
Schwarz et al.

[11] Patent Number: 5,232,447
[45] Date of Patent: Aug. 3, 1993

[54] NON-REUSABLE SYRINGE

[75] Inventors: Charles Schwarz; James D. Story, both of Austin, Tex.

[73] Assignee: JetFill, Inc., Austin, Tex.

[21] Appl. No.: 742,599

[22] Filed: Aug. 8, 1991

[51] Int. Cl.⁵ ............................................. A61M 5/00
[52] U.S. Cl. ................................. 604/110; 604/218; 604/228; 128/919
[58] Field of Search ............... 604/110, 187, 218, 220, 604/227, 207, 226, 228, 229; 346/140 R; 128/919

[56] References Cited

U.S. PATENT DOCUMENTS

| | | | |
|---|---|---|---|
| 1,961,490 | 6/1934 | Hein | 604/218 X |
| 2,554,352 | 5/1951 | Ward et al. | 604/200 X |
| 2,555,878 | 6/1951 | Drabicki | 604/228 |
| 2,619,087 | 11/1952 | Oclassen et al. | 604/220 |
| 2,856,923 | 10/1958 | Roger et al. | 604/226 |
| 2,860,635 | 11/1958 | Wilburn | 604/207 X |
| 2,959,170 | 11/1960 | Laub | 604/220 |
| 2,972,991 | 2/1961 | Burke | 604/228 X |
| 4,159,713 | 7/1979 | Prais | 604/228 X |
| 4,213,456 | 7/1980 | Böttger | 604/226 |
| 4,419,677 | 12/1983 | Kasugayama et al. | 346/140 R |
| 4,589,000 | 5/1986 | Koto et al. | 346/140 R |
| 4,613,326 | 9/1986 | Szware | 604/89 |
| 4,775,364 | 10/1991 | Alles . | |
| 4,775,369 | 10/1988 | Schwartz . | |
| 4,790,830 | 12/1988 | Hamacher | 604/274 |
| 4,850,968 | 7/1991 | Romanea . | |
| 4,862,427 | 9/1989 | Cocchi . | |
| 4,863,433 | 9/1989 | Payne . | |
| 4,874,372 | 10/1989 | McArthur . | |
| 4,911,693 | 5/1990 | Paris . | |
| 4,955,869 | 9/1990 | Bin . | |
| 4,976,702 | 12/1990 | Andrew . | |
| 5,037,393 | 8/1991 | Ellgass | 604/110 |
| 5,084,017 | 1/1992 | Maffetone | 604/110 |
| 5,116,320 | 5/1992 | Lo Duca | 604/110 |

FOREIGN PATENT DOCUMENTS

| | | | |
|---|---|---|---|
| 0112893 | 1/1969 | Denmark | 604/110 |
| 0395211 | 10/1990 | European Pat. Off. | 604/187 |
| 2622804 | 5/1989 | France | 604/218 |
| 2648715 | 12/1990 | France | 604/226 |
| 2197792 | 6/1988 | United Kingdom | 604/110 |

Primary Examiner—C. Fred Rosenbaum
Assistant Examiner—Mark O. Polutta
Attorney, Agent, or Firm—Cox & Smith Incorporated

[57] ABSTRACT

A liquid dispensing syringe having a plunger unit that is non-retractable after liquid is dispensed. The syringe is only refillable by persons having special filling equipment.

1 Claim, 1 Drawing Sheet

NON-REUSABLE SYRINGE

BACKGROUND OF THE INVENTION

1. Field of the Invention

The present invention relates in general to liquid dispensing syringes. In particular the present invention prevents the reuse of a syringe except by persons having filling equipment.

2. Background Description

The idea of a simple safety recyclable syringe has been the subject of many patents due to the health concerns caused by the threat of hepatitis, AIDS, and drug use. As a result of these concerns, non-reusable syringes have been designed. Quite often, that design idea requires a syringe that must meet demanding requirements which often results in a more complicated and expensive syringe to produce, as disclosed by U.S. Pat. No. 4,863,427 to Cocchi. Cocchi's patent utilizes numerous and complicated components such as links, tie rods, and or locking mechanisms.

The present invention works on a simpler principle. It places the plunger unit in a position that makes it unable to be grasped or withdrawn after the plunger unit has ejected the internal fluid, thereby rendering it unrefillable and useless to the end user. The present invention does not make use of chemically active materials that may produce unforeseen and unwanted reactions with the fluids intended for injection. The disclosure in U.S. Pat. No. 4,874,372 to McArthur works by reacting an internal connector material with the intended injection fluid, thereby causing the connector material to loose its structural integrity and render it useless.

The plunger unit portion of the present invention is positioned below the open end of the syringe in the empty position, thereby rendering the syringe virtually useless because the plunger unit cannot be grasped and subsequently withdrawn and filled by vacuum action. The prior art syringes require the plunger to be withdrawn for an intake stroke of fluid. When the present invention is in the empty position, the use of positive pressure applied to the closed end of the plunger unit is required to refill the syringe. Thus, by removing the filling ability from the syringe, only those who possess positive displacement filling equipment may refill the syringe. Essentially, the ability of filling syringes has been removed from the end user and passed on to a dedicated filling machine which can be more strictly controlled. The syringe of the present invention can be used and reused with the aid of a filling type apparatus.

The prior art does not disclose recyclability of syringes. The syringes of the prior art, U.S. Pat. No. 4,850,968 to Romano, U.S. Pat. No. 4,775,364 to Alles, U.S. Pat. No. 4,955,869 to Bin, and U.S. Pat. No. 4,863,433 to Payne, are all destroyed after one use and cannot be recycled even by those who possess machinery expressly designed for the filling of syringes. The prior art syringes utilize a plunger that is withdrawn for an intake stroke of liquid. One end of the plunger must connect to a seal and the other extends longitudinally past the open end of the syringe body. This results in prior art syringes being less compact, less durable, and less easily packaged as compared to the present invention and is especially evident when the syringes are packaged in the prefilled condition.

SUMMARY OF THE INVENTION

The present invention prevents the reuse of a syringe in dispensing of liquids. Once the liquid is dispensed refilling the non-reusable syringe is not possible by the user without special equipment.

The present invention comprises a cylindrically shaped hollow tube or barrel having an open end and a conical wall formed on the other end defining a reduced diameter hollow axial protuberance. That protuberance may be tapered to accommodate a syringe needle. The open end of the tube has a pair of integral finger grippable ears that aid in operating the non-reusable syringe.

A plunger unit is provided having a cylindrically shaped body that has one end closed forming a generally radial top surface. The other end of the plunger unit has an imperforate surface that conforms to the conical shape of the closed end of the tube. The plunger unit is telescopically and sealably insertable into the open end of the tube. The plunger unit also has an axial length dimensioned such that the top portion of the plunger unit, engagable by the thumb of the user, is substantially above the open end of the tube when that tube is filled with a liquid. The plunger unit has an integral outwardly projecting annular sealing shoulder in contact with the inner wall of the hollow tube, thus sealing the liquid within the tube. The liquid within the tube is prevented from escaping through the opening in the syringe needle tip by a cover that is placed over the needle. That cover is removed prior to use of the present invention.

The preferred method of use for the present invention is to manually apply axial pressure to the plunger unit, thereby forcing liquid contained in the liquid chamber out through the syringe needle tip. Once all the liquid is dispensed from the tube, the top end of the plunger unit will reside below the open end of the non-reusable syringe. Hence, the plunger unit is not removable without special filling equipment, therefore, the syringe of the present invention is not user refillable.

Accordingly, several objects and advantages of the syringe embodying this invention are:

(a) To provide a simple, safe syringe that is non-reusable. Once the plunger unit is depressed, it can only be retracted through positive displacement provided by a filling machine. Such syringes or the like can be refilled by manufacturers that have the proper filling equipment.

(b) To provide a simple safe syringe that is compact and rugged, having a long shelf life, and is easy to package in a prefilled state. Prior art designs required a plunger that was capable of being withdrawn for an intake stroke of liquid. The plunger was required to have sufficient length or an appendage so as to extend longitudinally beyond the end of the syringe body. As a result, the syringe becomes longer, more bulky, and more fragile to package, especially when in a prefilled condition as compared to a syringe embodying present invention.

(c) To provide a simple, safe non-reusable syringe that is inexpensive to produce and assemble. It can be fabricated using injection molding machines. Most of the prior art syringes require more complex and expensive production molds, machinery, techniques, and labor to produce more fragile and complex components.

(d) To provide a simple, safe non-reusable syringe with few parts, thereby increasing reliability, safety, ease of manufacturing, and ease of use to end user.

(e) To provide a simple safe non-reusable syringe that is chemically inert and safe. The present invention does not require the use of any chemical reactions to render it non-reusable to its users.

A more complete appreciation of the invention and many of the attendant advantages thereof will be readily perceived as the same becomes better understood by reference to the following detailed description when considered in connection with the following drawings.

DETAILED DESCRIPTION OF PREFERRED EMBODIMENT

Figure 1:
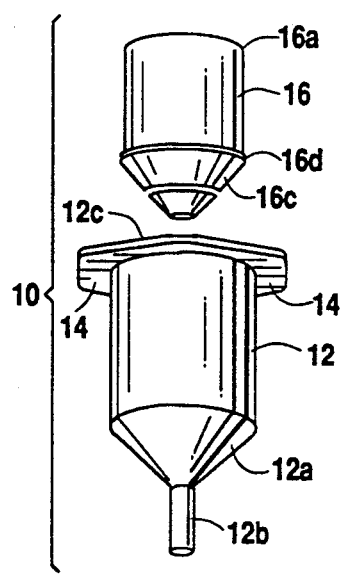
FIG. 1 is an exploded perspective view of the elements from which a syringe embodying this invention is assembled.

Referring to FIG. 1, a non-reusable syringe is shown generally at 10. The non-reusable syringe 10 is preferably embodied in an injection molded, cylindrically shaped hollow tube 12. The hollow tube 12 has a conical wall 12a that defines an axial protuberance 12b. Protuberance 12b may be tapered to accommodate the tapered portion of a syringe needle. Although the non-reusable syringe 10 is shown without a syringe needle being attached, a syringe needle may be attached if desired. The syringe 10 further comprises an integrally formed pair of finger grippable ears 14 that are adjacent to the open end 12c of the hollow tube 12. The finger grippable ears 14 aid in the holding the non-reusable syringe 10 when axial pressure is applied to the plunger unit by the thumb of the user.

A plunger unit 16 is provided, having a cylindrically shaped body that has one end closed, forming a generally radial top surface 16a that has a thumb rest indentation 16b. The thumb rest 16b in conjunction with the finger grippable ears 14 aid in operating syringe 10.

The other end of the plunger unit 16 has an imperforate surface 16c that conforms to the conical shape 12a of the closed end of tube 12. The plunger unit 16 also has an annular external sealing shoulder 16d that will sealably contact the inner wall of tube 12 when the plunger unit 16 is slidably inserted into the open end 12c of tube 12. The plunger unit 16 also has an axial length dimensioned such that the top surface 16a of the plunger unit 16 is substantially above the open end 12c of tube 12 when tube 12 is filled with a liquid charge 20.

Figure 5:
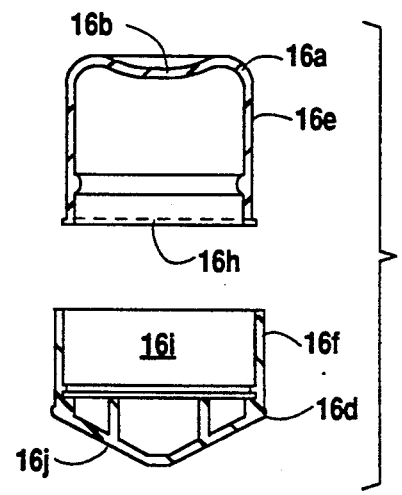
FIG. 5 is a sectional view of the plunger sub-units.

The plunger unit may be fabricated in two telescopically related sub-units, namely, a manual actuator subnit 16e and a plunger sub-unit 16f, as shown in FIG. 5. The manual actuator sub-unit 16e preferably is formed in an injection molded cylindrically shaped hollow body. That hollow body has an open end 16h and a closed end 16a. The closed end 16a has a small indentation that is utilized as a thumb rest 16b. The manual actuator sub-unit 16e is slidably insertable into plunger sub-unit 16f which has a cylindrically shaped hollow body with its top end 16i open to receive the manual actuator sub-unit 16e. The other end 16j of plunger sub-unit 16f is conically closed to cooperate with the conically closed end of 12a of tube 12.

Figure 2:
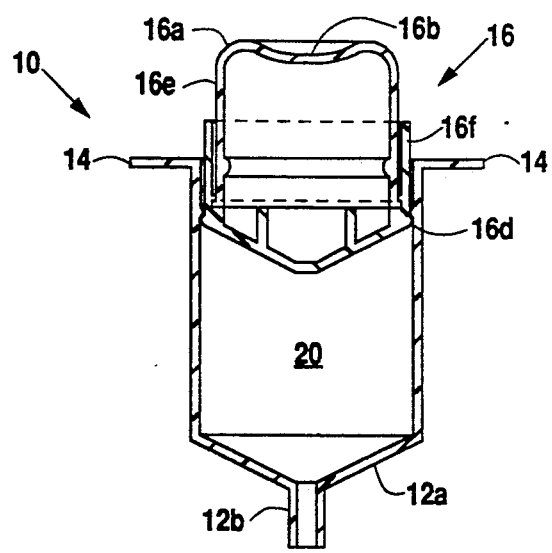
FIG. 2 is a sectional view of the assembled syringe elements when filled with a liquid.

As shown in FIG. 2, the manual actuator sub-unit 16e make an abutting connection to plunger sub-unit 16f. FIG. 2 also illustrates the plunger unit 16 after it has been inserted into tube 12. When tube 12 is filled with a liquid charge 20, the top portion of the plunger unit 16 is positioned substantially above the opened end 12c of tube 12 as illustrated. The plunger unit 16 is downwardly movable by thumb pressure, thereby forcing the liquid charge 20 out of tube 12 through the hollow axial protuberance 12b.

Figure 3:
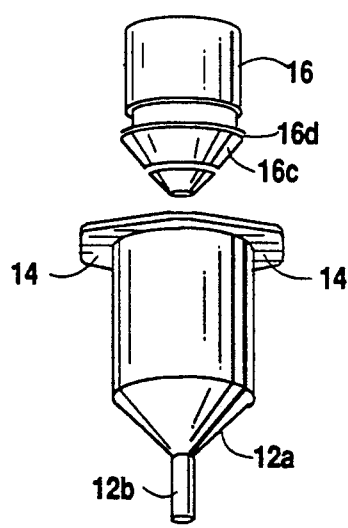
FIG. 3 is a sectional view of the assembled syringe elements after all liquid has been discharged.

FIG. 3 illustrates a second position of the plunger unit 16 after all the liquid charge 20 is forced from tube 12. The bottom surface of plunger unit 16 conforms to the shape of the closure formed at the bottom of tube 12. Once the liquid charge 20 has been forced from tube 12, the top portion of the plunger unit 16 is below the open end 12c of tube 12. Thus, plunger unit 16 is non-retractable by the user, without special equipment, particularly when fabricated as two abutting sub-units 16e and 16f.

Figure 4:
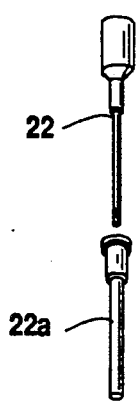
FIG. 4 is an exploded perspective illustration of modified syringe elements with a needle attached.

FIG. 4 illustrates the non-reusable syringe 10 with a syringe needle 22 attached to the axial hollow protuberance 12b. The syringe needle 22 has a cover 22a positioned to cover needle 22 when syringe 10 is filled with the liquid charge 20. FIG. 4 also illustrates an alternate method of assembly of the manual actuator sub-unit 16e and plunger sub-unit 16f. The plunger sub-unit 16f is fabricated with a diameter permitting it to slide into the open end of manual actuator sub-unit 16e. Both manual actuator sub-unit 16e and plunger sub-unit 16f are slidable insertable into the open end of tube 12, with sealing shoulder 16d engaging the inner wall of tube 12.

We claim:

1. A liquid dispensing syringe, comprising;
    a cylindrically shaped hollow tube having one open end;
    said tube having an inner wall defining a liquid chamber;
    said tube having a conically shaped closure on the end located oppositely to said open end;
    said closure defining a hollow tapered syringe needle mounting;
    a plunger having a cylindrically shaped hollow body open at one end and conically closed on the end located oppositely to said open end;
    said plunger having an outwardly projecting annular shoulder sealably engagable with said inner wall of said hollow tube when said plunger is slidably inserted into said open end of said tube;
    said conically closed end cooperating with said conically shaped closure to force liquid through said needle mounting;
    an actuator having a cylindrically shaped hollow body open at one end and closed on the end located oppositely said open end;
    said actuators closed end having a generally radial top surface contoured to be engagable by the thumb of the user;
    said actuator open end being slidably insertable into said open end of said plunger and abuttingly engagable with said plunger;
    said actuator's closed end extending above said open end of said tube in a first position when said tube contains liquid;
    said actuator's closed end being movable to a second position below said open end of said tube when applied axial pressure to said actuator forces said liquid from said tube; and
    said actuator and plunger being returned to said first position by the positive pressure introduction of liquid through said needle mounting.

* * * * *